United States Patent [19]

Anderson et al.

[11] 4,025,321

[45] May 24, 1977

[54] PURIFICATION OF NATURAL GAS STREAMS CONTAINING OXYGEN

[75] Inventors: Richard Alan Anderson, Katonah; Karl Gardner Davis, Suffern; Ervine Stout Holmes, Yorktown Heights, all of N.Y.

[73] Assignee: Union Carbide Corporation, New York, N.Y.

[22] Filed: Sept. 30, 1975

[21] Appl. No.: 618,062

[52] U.S. Cl. .................................. 55/33; 55/62; 55/73; 55/75; 423/219
[51] Int. Cl.² ........................................ B01D 53/04
[58] Field of Search ............... 55/33, 62, 75, 73; 260/676 AD; 423/219

[56] References Cited

UNITED STATES PATENTS

| 2,924,504 | 2/1960 | Reitmeier | 423/219 X |
|---|---|---|---|
| 3,023,841 | 3/1962 | Milton et al. | 55/75 X |
| 3,094,569 | 6/1963 | Thomas | 55/75 X |
| 3,841,058 | 10/1974 | Templeman | 55/75 X |
| 3,864,452 | 2/1975 | Chi et al. | 55/75 X |

*Primary Examiner*—Frank A. Spear, Jr.
*Assistant Examiner*—Robert H. Spitzer
*Attorney, Agent, or Firm*—Richard G. Miller

[57] ABSTRACT

Hydrocarbon gas streams containing small quantities of molecular oxygen are found to adversely affect the adsorptive characteristics of zeolite adsorbent beds at temperatures above 350° F. Problem is avoided by converting the oxygen to readily sorbable compounds prior to contacting the bed with the gas stream.

5 Claims, 1 Drawing Figure

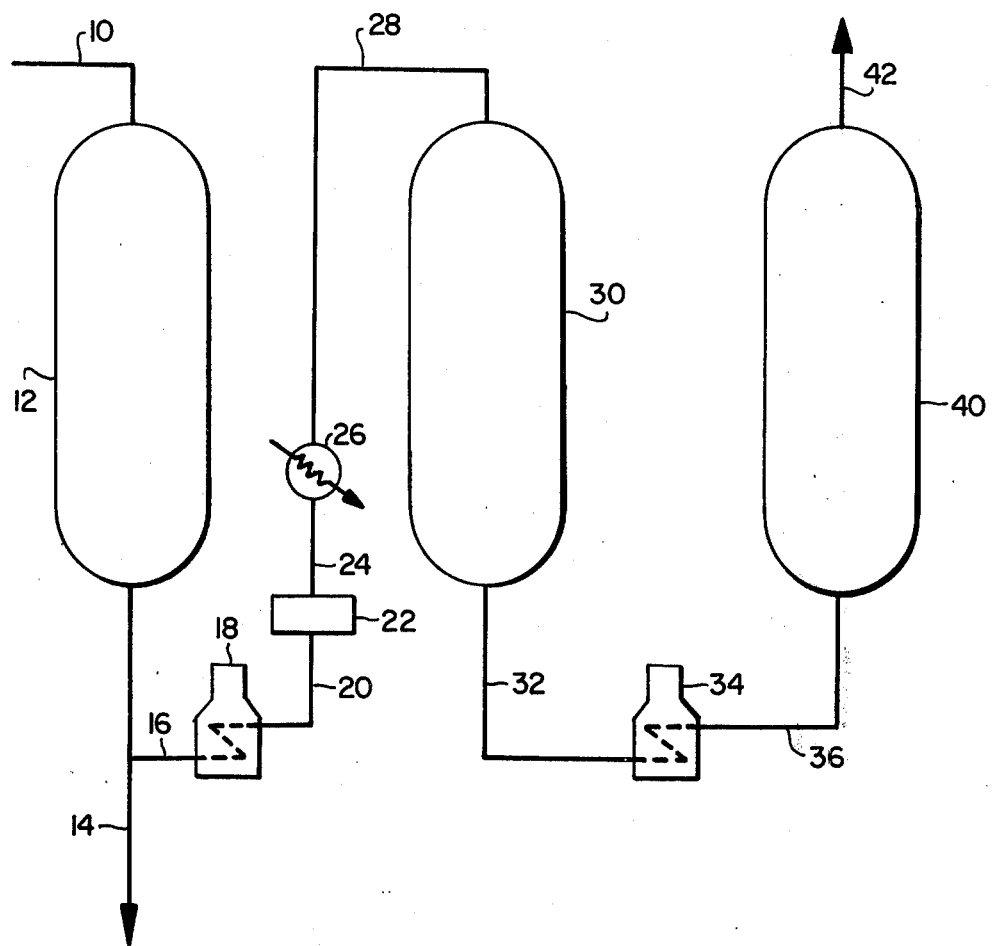

PURIFICATION OF NATURAL GAS STREAMS CONTAINING OXYGEN

The present invention relates in general to the purification of hydrocarbon fluid streams and more particularly to the purification of hydrocarbon fluid streams which contain from 10 ppm to 10,000 ppm oxygen impurity in addition to one or more other impurities such as water, carbon dioxide and sulfur compounds.

The purification of a wide variety of hydrocarbon feedstocks using zeolitic molecular sieves to selectively adsorb the impurity has in recent years become a common practice. Most petroleum crudes contain more than tolerable amounts of sulfur impurities which must be removed in conjunction with one or more refining operation before the refined product is ultimately consumed. Natural gas, in addition to sulfur compound impurities can also contain unacceptably high amounts of water vapor and carbon dioxide. Thus whether the feedstock is in the liquid phase or the gas phase, selectively adsorption processes have been developed to reduce the impurity content to levels compatible with the intended end use of the product.

Most commonly the adsorption process utilizes one or more fixed beds or molecular sieve adsorbent through which the feedstock is passed and the impurity is retained. Flow-through of the feedstock is terminated before breakthrough of the adsorbable impurity and thereafter the bed is regenerated by countercurrent hot purge desorption and subsequent cool-down with a minor portion of the purified product or some other available purge fluid essentially free of sorbable constituents undesirably in the purified feedstock product.

Although not ordinarily considered a significant impurity, oxygen is frequently found in relatively small concentrations in either the hydrocarbon feedstocks being purified or in the hydrocarbon purge fluid or in both. Being non-condensible at temperature and pressure conditions used to liquify hydrocarbon gas stream and being essentially non-sorbable on molecular sieves under the conditions prevailing in adsorption purification processes for hydrocarbons, the oxygen present in most hydrocarbons has been largely ignored. It is found, however, that a number of problems can be created by the presence of oxygen in hydrocarbon fluids treated in contact with molecular sieves, even if present in amounts as low as 10 ppm.

For a variety of reasons, natural gas quite frequently contains some gaseous oxygen, and can contain as much as 10,000 parts per million (volume). Usually amounts greater than 500 ppm are found in natural gas obtained from low pressure or sub-atmospheric pressure gas fields. In pipeline natural gas some oxygen is doubtlessly introduced during pipeline hydrotesting, during in ground, i.e., cavern, storage and during periodic compression along the pipeline.

In treating oxygen-containing hydrocarbon feedstocks, e.g. natural gas, to remove other impurities, the oxygen can interfere with the adsorption-purification process in a number of ways, depending on the concentration of the oxygen, the temperature of the adsorption system and the presence of sulfur compounds. At temperatures about 150° F, oxygen reacts appreciably with sulfur compounds such as $H_2S$ and mercaptans to produce sulfur and water as principal reaction products. These substances are strongly held on the zeolite surfaces and seriously affect the capacity of the adsorbent bed to retain the impurities desired to be removed from the feedstock being treated. Sulfur is especially harmful in this regard. In the absence of sulfur compounds, at operating temperatures of 350° F. and higher, oxygen is still a problem in hydrocarbon feedstocks since it reacts appreciably with hydrocarbons to form water, oxygenated organic compounds and/or carbon dioxide. These reaction products are, in part, formed in the adsorption bed ahead of the impurities mass transfer zones and are thus to some extent purged from the bed into the purified product stream before the normal termination of the adsorption stroke in the bed. Purity specifications for the product stream are thereby adversely affected.

It is frequently the case that adsorption purification processes employ temperatures below 150° F. during the adsorption step, and hence most of the above-mentioned problems are not encountered in that stage of the overall process. In regenerating the bed in preparation for the next adsorption step, however, the purge-desorption step must be accomplished at temperatures at least higher than 150° F. and preferably at temperatures higher than 350° F. in order to avoid the need for unduly large quantities of purge gas. Accordingly, where the purge gas is a non-sorbable hydrocarbon, such as purified natural gas, and contains from 10 to 10,000 ppm (volume) of $O_2$, the aforesaid harmful effects due to the presence of oxygen are encountered. For example, when a molecular sieve adsorption purification is employed to remove carbon dioxide from a fluid which is to be treated cryogenically below the freezing point of carbon dioxide for liquefaction of some or all of the purified stream, the water generated by oxygen impurity in the hot purge fluid and deposited on the adsorbent reduces the adsorbent's capacity for carbon dioxide. Thus deleterious levels of both water and carbon dioxide pass into the cryogenic unit causing plugging problems.

Having recognized the problems and their source, we have discovered a method for solving same without the need for supplemental adsorption apparatus and without removing all sorbable impurities from the hydrocarbon purge gas stream.

In accordance with a generic embodiment of the process of the present invention a hydrocarbon feedstock containing at least one sorbable impurity selected from the group consisting of water, carbon dioxide, hydrogen sulfide and alkyl mercaptan is passed through a first fixed bed of activated zeolitic molecular sieve having pore diameters large enough to adsorb the said impurity, with the proviso that the said fixed bed is at a temperature of less than 150° F. when said hydrocarbon feedstock also contains from 10 to 10,000 ppm (volume) of gaseous oxygen, terminating the passage of the feedstock through the bed prior to breakthrough of the impurity adsorbed therein, thereafter desorbing and removing the adsorbed impurity from said first bed by purging same counter-currently with a non-sorbable hydrocarbon purge gas previously containing from 10 to 10,000 ppm by volume of molecular oxygen, said oxygen-containing hydrocarbon purge gas stream having been treated by the steps of (a) reducing the elemental oxygen content thereof by reacting the oxygen with hydrocarbon molecules comprising the said gas stream, preferably by heterogeneous catalysis in contact with an oxygenation catalyst mass in the solid state, and (b) passing the oxygen-depleted hydrocarbon gas stream together with at least some of the oxygen-containing reaction products produced in situ therein through a second fixed bed of activated zeolitic molecular sieve adsorbent, the temperature of the gas stream being less than 350° F., preferably less than 150° F. and said molecular sieve bed being at a temperature of greater than 350° F.

The species of molecular sieve adsorbent employed in the adsorbent beds of the present process are well known in the art and are not critical factors. It is necessary only that the pores of the adsorbent are large enough to adsorb the impurity components of the feedstock hydrocarbon being treated and the oxygen-containing reaction products produced in the purge gas stream. The calcium form of zeolite A, described in detail in U.S. Pat. No. 2,882,243, has a high capacity for the adsorption of water and carbon dioxide and is advantageously employed.

The hydrocarbon feedstock treated can be any of those commonly involved in petroleum refining operations and in some aspects of petroleum production. Natural gas streams are ideally suited for treatment by the present process. In the purification-adsorption step of the process the feedstock can be in the liquid or in the vapor state.

The hydrocarbon gas stream which is treated so that it can be used to hot purge desorb the impurity-laden adsorbent can be any oxygen-containing hydrocarbon stream in which the principal hydrocarbons are non-sorbable, i.e. are less strongly adsorbed in the inner adsorption cavities of the molecular sieve adsorbent than the least strongly adsorbed impurity to be removed from the feedstock being purified. It is to be understood that molecules which are excluded from the inner adsorption cavities of a molecular sieve species by virtue of the pore diameters of thereof are considered to be less strongly sorbable on that zeolite species than smaller molecules which can pass through the zeolite pores even though the larger molecules may be more strongly held than the smaller ones in zeolites having pores large enough to adsorb both molecular species. Thus methane, ethane and n-butane can be used to purge $CO_2$ impurity from a zeolite adsorbent having pore diameters not greater than 4 Angstroms, whereas methane, ethane and iso-butane can be used to purge $CO_2$ from a molecular sieve having pore diameters of 5 Angstroms or less. Large concentrations of hydrogen, nitrogen and inert gases can be tolerated in the purge gas stream. Most commonly when the feedstock is natural gas, the purge gas will be natural gas from which the water, carbon dioxide and sulfur compounds have been removed, or a comparable gas stream consisting essentially of methane.

In reacting the oxygen of the purge gas stream precursor with hydrocarbon constituents thereof, the precise means employed are not critical to the present process. Elevated temperatures alone are sufficient to accomplish the desired results, but a more efficient method is the use of any of the numerous oxygenation catalyst material commercially available. Especially effective are the copper, manganese and iron compound catalyst systems described in detail in U.S. Pat. No. 3,361,531, and similar oxide compositions described in Boreskov, G.K. "Mechanism of Catalytic Oxidation Reactions on Solid Oxide Catalysts" *Kinetica i Kataliz*, Vol 14, No. 1, p. 7, Jan—Feb 1973. issued Jan. 2, 1968, the entire disclosure of which are incorporated herein by reference.

In its generic aspect, the present invention not only converts an unsuitable purge gas stream to an entirely satisfactory one, but also in the treatment of the gas stream there is provided the added advantage that a hot previously regenerated adsorbent bed is cooled down to adsorption stroke temperature and much of the heat energy therefrom is transferred to the purge desorbing of another bed using the newly purified purge gas stream. These advantages are realized to a high degree in a more specific process embodiment of this invention in which at least three fixed adsorption beds are used cyclically for the purification of natural gas streams. In such an embodiment a natural gas feedstock (a) containing at least one sorbable impurity selected from water, carbon dioxide, hydrogen sulfide and alkyl mercaptan, and containing as a non-sorbable impurity from 10 to 10,000 ppm (volume) of entrained oxygen is passed at a temperature below 150° F. through a first fixed bed of activated zeolitic molecular sieve having pore diameters large enough to adsorb the said sorbable impurity of said feedstock and recover a purified feedstock product containing at least 10 ppm (volume) of oxygen, terminating the passage of the feedstock (a) through the bed prior to breakthrough of the impurity adsorbed therein, reacting the oxygen in a portion of the recovered purified feedstock with hydrocarbon molecules comprising same to form carbon dioxide and water and to reduce the oxygen concentration thereof, preferably to less than 10 ppm (volume), thereafter passing at a temperature below 350° F. the resulting oxygen-depleted hydrocarbon gas stream (b) containing reaction products formed in situ therein through a second fixed adsorbent bed containing zeolitic molecular sieve adsorbent having pore diameter of at least 4 Angstroms, said second fixed bed being at a temperature higher than 350° F. as a result of being hot purged with natural gas stream substantially free of $CO_2$, $H_2S$ and $H_2O$, recovering the heated and substantially $CO_2$ and $H_2O$-free hydrocarbon effluent (c) from said second fixed bed and passing same as a purge gas at a temperature of greater than 350° F. through a third fixed adsorbent bed containing zeolitic molecular sieve adsorbent having adsorbed thereon impurity constituents as a result of passage therethrough of the said natural gas feedstock (a) the direction of flow of said purge gas (c) from the said second bed through said third bed being countercurrent to the direction of passage of natural gas feedstock (a) through said third bed, and thereafter passing said natural gas feedstock (a) through said second bed in a direction co-current to the passage of oxygen-depleted hydrocarbon gas stream (b) therethrough.

The present invention is illustrated by the following description taken in conjunction with the drawings.

In the drawings the FIGURE is a schematic flow diagram of a three-bed adsorption purification system in which each of the three beds cyclically undergoes the steps of adsorption, countercurrent hot purge desorption and co-current cool down. Operation of the process is such that at any given time all three steps are in progress with each step being carried out in a different bed. The conventional valving and conduit connections which enables cycling of the process steps in each bed are not shown in the drawings.

Natural gas which contains 1.5 volume-% carbon dioxide and 150 ppm (volume) $H_2O$ and 50 ppm (volume) oxygen is purified in an adsorption system comprising three fixed adsorption beds, each containing 35,000 pounds of type 4A molecular sieve. With reference to the drawing, the natural gas feedstock is passed at the rate 32.5 million standard cubic feet per day through line 10 at a temperature of 85° F. and at a pressure of 600 psi. In passage through bed 12 carbon dioxide and water are adsorbed and the effluent product gas stream through line 14 contains less than 50 ppm $CO_2$, less than 1 ppm $H_2O$ and essentially the same concentration entrained oxygen present in the feedstock. A slipstream of product gas is removed from line 14 via line 16 at the rate of 17.4 million standard cubic feet per day, heated to 400° F. in furnace 18 and passed through line 20 to catalytic oxidation unit 22. The catalyst mass in unit 22 consists of cuprous oxide dispersed on synthetic mordenite having an $SiO_2/Al_2O_3$ molar ratio of 11.2, and converts sufficient oxygen of the gas stream to $CO_2$ and $H_2O$ to lower the entrained oxygen content to less than 10 ppm (volume). The effluent gas stream carrying the product $CO_2$ and $H_2O$ is passed via line 24 through cooler 26 wherein the temperature of the effluent is reduced to about 100° F. and thereafter is fed through line 28 into adsorption bed 30. Previously bed 30 had been utilized to purify a portion of the same feedstock as currently is being treated in bed 12. Bed 30 has also been hot purge desorbed at a temperature of 500° F. in a direction counter-current to the flow of the feedstock stream and the cooling oxygen-depleted gas stream currently flowing through line 28. In its passage through bed 30, the gas stream from cooler 26 through line 28 deposits $CO_2$ and $H_2O$ as adsorbates on the ingress end of the bed in a well defined adsorption zone, cools the bed 30 along an advancing cold front, and is itself heated to approximately 500° F. This effluent hot, dry and essentially $CO_2$-free gas stream is passed via line 32 to furnace 34, wherein it is heated to 600° F. and thereafter fed through line 36 through adsorption bed 40. Bed 40 has previously been employed to purify, in a direction counter-current to the direction of flow of the present gas stream, a portion of the same feedstock as is currently being treated in bed 12, and is loaded with adsorbed $CO_2$ and $H_2O$ impurities. Bed 40 is regenerated and heated by the passage therethrough of the purging gas stream from line 36 and the desorbed $CO_2$ and $H_2O$ is passed through line 42 for disposal.

What is claimed is:

1. Process for purifying a hydrocarbon feedstock containing at least one sorbable impurity selected from the group consisting of water, carbon dioxide hydrogen sulfide and alkyl mercaptan which comprises passing said feedstock through a first fixed bed of activated zeolitic molecular sieve having pore diameters large enough to adsorb the said impurity, with the proviso that the said fixed bed is at a temperature of less than 150° F. when said hydrocarbon feedstock also contains from 10 to 10,000 ppm by volume of gaseous oxygen, terminating the passage of the feedstock through the bed prior to breakthrough of the impurity adsorbed therein, thereafter desorbing and removing the adsorbed impurity from said first bed by purging same counter-currently with a non-sorbable hydrocarbon purge gas previously containing from 10 to 10,000 ppm by volume of molecular oxygen, said oxygen-containing hydrocarbon purge gas stream having been treated by the steps of (a) reducing the said oxygen content thereof by reacting the oxygen with hydrocarbon molecules comprising the said gas stream, and (b) passing the oxygen-depleted hydrocarbon gas stream together with at least some of the oxygen-containing reaction products produced in situ therein through a second fixed bed of activated zeolitic molecular sieve adsorbent, the temperature of the gas stream being less than 350° F., and said molecular sieve bed being at a temperature of greater than 350° F.

2. Process according to claim 1 wherein the initial oxygen content of the non-sorbable hydrocarbon purge gas stream is reduced by reacting said oxygen with hydrocarbon molecules in contact with an oxidation catalyst mass in the solid state.

3. Process according to claim 1 wherein the hydrocarbon feedstock being purified is natural gas.

4. Process according to claim 3 wherein a portion of the feedstock after passage thereof through the first adsorption bed, is utilized as the purge gas stream after treatment to decrease etc. oxygen content.

5. Process for purifying a natural gas feedstock, (a) containing at least one sorbable impurity selected from water, carbon dioxide, hydrogen sulfide and alkyl mercaptan, and containing as a non-sorbable impurity from 10 to 10,000 ppm by volume of gaseous oxygen, which comprises passing said stream (a) at a temperature below 150° F. through a first fixed bed of activated zeolitic molecular sieve, having pore diameters large enough to adsorb the said sorbable impurity of said feedstock (a) terminating the passage of the feedstock (a) through the bed prior to breakthrough of the impurity adsorbed therein, reacting the oxygen in a portion of the recovered purified feedstock with hydrocarbon molecules comprising same to form carbon dioxide and water and to reduce the oxygen concentration thereof, thereafter passing at a temperature below 350° F. the resulting oxygen-depleted hydrocarbon gas stream (b) containing reaction products formed in situ therein through a second fixed adsorbent bed containing zeolitic molecular sieve adsorbent having pore diameter of at least 4 Angstroms, said second fixed bed being at a temperature higher than 350° F. as a result of being hot purged with natural gas stream substantially free of $CO_2$, $H_2S$ AND $H_2O$, recovering the heated and substantially $CO_2$ and $H_2O$-free hydrocarbon effluents (c) from said second fixed bed and passing same as a purge gas at a temperature of greater than 350° F. through a third fixed adsorbent bed containing zeolitic molecular sieve adsorbent having adsorbed thereon impurity constituents as a result of passage therethrough of the said natural gas feedstock (a) the direction of flow of said purge gas (c) from the said second bed through said third bed being countercurrent to the direction of passage of natural gas feedstock (a) through said third bed, and thereafter passing said natural gas feedstock (a) through said second bed in a direction co-current to the passage of oxygen-depleted hydrocarbon gas stream (b) therethrough.

* * * * *